(12) United States Patent  (10) Patent No.: US 7,910,359 B2
Ricordi  (45) Date of Patent: Mar. 22, 2011

(54) HYBRID DEVICE FOR CELL THERAPIES

(75) Inventor: Camillo Ricordi, Miami, FL (US)

(73) Assignee: University of Miami, Miami, FL (US)

( * ) Notice: Subject to any disclaimer, the term of this patent is extended or adjusted under 35 U.S.C. 154(b) by 430 days.

(21) Appl. No.: 11/185,011

(22) Filed: Jul. 20, 2005

(65) Prior Publication Data

US 2006/0024276 A1    Feb. 2, 2006

Related U.S. Application Data

(60) Provisional application No. 60/591,919, filed on Jul. 29, 2004.

(51) Int. Cl.
 *A61M 5/14* (2006.01)
(52) U.S. Cl. .................. 435/297.2; 604/891.1; 435/177; 435/284.1; 435/286.4; 424/422
(58) Field of Classification Search .................. None
See application file for complete search history.

(56) References Cited

U.S. PATENT DOCUMENTS

| 4,618,586 A | 10/1986 | Walker |
| 5,100,392 A | 3/1992 | Orth et al. |
| 5,116,494 A | 5/1992 | Chick et al. |
| 5,324,518 A | 6/1994 | Orth et al. |
| 5,569,462 A | 10/1996 | Martinson et al. |
| 5,614,205 A | 3/1997 | Usala |
| 5,725,854 A | 3/1998 | Selawry |
| 5,798,113 A | 8/1998 | Dionne et al. |
| 5,800,828 A | 9/1998 | Dionne et al. |
| 5,800,829 A | 9/1998 | Dionne et al. |
| 5,834,001 A | 11/1998 | Dionne et al. |
| 5,869,077 A | 2/1999 | Dionne et al. |
| 5,871,767 A | 2/1999 | Dionne et al. |
| 5,874,099 A | 2/1999 | Dionne et al. |
| 6,083,523 A | 7/2000 | Dionne et al. |
| 6,322,804 B1 | 11/2001 | Dionne et al. |
| 6,503,273 B1 | 1/2003 | McAllister et al. |
| 6,630,154 B1 | 10/2003 | Fraker et al. |
| 6,642,019 B1 | 11/2003 | Anderson et al. |
| 6,716,246 B1 | 4/2004 | Gonzalez |

FOREIGN PATENT DOCUMENTS

| CA | 2 355 675 | 6/2001 |
| JP | 2-211170 | 8/1990 |
| RU | 2143867 | 1/2000 |
| WO | WO91/08783 | 6/1991 |
| WO | WO 00/35371 | 6/2000 |

*Primary Examiner* — Allison M Ford
(74) *Attorney, Agent, or Firm* — Ropes & Gray LLP; Barbara A. Ruskin; Wyan-Ching M. Lee

(57) ABSTRACT

A device for receiving implanted biological material includes a porous outer wall defining an inner space, a fluid manifold assembly for selectively infusing at least one of immunosuppressive and growth factor media to said space, and a pump structure operatively coupled to the manifold assembly. The device may comprise an additional plunger body for being disposed in said space and so as to define a peripheral gap between the plunger and the perforated wall of the device.

36 Claims, 3 Drawing Sheets

HYBRID DEVICE FOR CELL THERAPIES

This application claims the benefit of U.S. Provisional Application No. 60/591,919, which was filed Jul. 29, 2004, the disclosure of which is incorporated herein by this reference.

PCT Application No. PCT/MX99/00039, published as PCT Publication WO 00/35371, the entire disclosure of which is incorporated herein by this reference, discloses a device for xenotransplantation of islet-sertoli cell mixtures. This is a device in which new capillaries are allowed to grow through a cylindrical, perforated metal mesh, which contains a non-completely occluded plastic (e.g., Teflon) plunger. An open space of approximately 1 mm is defined between the plunger and the mesh to allow for new capillaries to grow through the external wall of the device, providing a vascular bed between the plunger and the mesh. After some time (4-8 weeks), the plunger is removed and the selected cells for transplant are deposited in its stead.

BACKGROUND OF THE INVENTION

The availability of a capillary bed in close proximity to the implanted cells, in an exemplary case islet cell clusters, is disclosed as promoting engraftment of the cellular transplant. Furthermore the presence of the co-transplanted sertoli cells is thought to confer immunoprotection/immunomodulation within the device. Sertoli cells are derived from the testis and express FasL (Fas ligand). These cells are thought to be able to confer local immunoprotection and in the case of the testis microenvironment, allow for prolonged survival of other cell types transplanted into the testis. Intratesticulat transplantation of cells such as islets, or co-transplantation of islets with sertoli cells has been attempted for the past two decades, with the objective to confer immunoprotection from the immune-attack of the transplanted cells by the recipient immune system.

SUMMARY OF THE INVENTION

While the above-described approach has potential advantages, according to the system design, the implanted cells can still be recognized by the recipient's system as non-self, foreign live biologic tissues, and therefore will be subject to an immune response that in the case of a xenograft (transplant of tissue between different species) will be particularly strong. The result is that the implanted cells will be attacked as foreign tissues and even co-transplantation of sertoli cells may not be sufficient to protect the therapeutic cells type. Thus, powerful systemic immunosuppression of the patient may nevertheless be required, especially in the case of transplantation between species such as pig to human. Moreover, a potential disadvantage of the above-proposed cylindrical device is that the deposited cylindrical column of cells will be too thick for the nutrients from the new capillaries to reach the more inwardly disposed cells, before the full thickness of the cellular implant will be fully vascularized by the peripheral capillary bed, so that these cells may not thrive and/or only a small portion of the implanted cells may survive until adequate re-vascularization occurs.

It is an object of the invention to avoid the requirement for long term systemic immunosuppression of recipients of cellular transplants, which currently limits the applicability of such procedures to the most severe cases of disease state for which the cellular therapy is indicated (e.g., hypoglycemia unawareness and labile diabetes in the case of insulin dependent diabetes).

It is also an object of the invention to provide an assembly that facilitates the addition of factors to favor engraftment and function of the transplanted cells and tissues, before, during and after re-vascularization of the cellular implant. It is a further object of the invention to provide a receptacle for the cellular/tissue transplant that favors cellular survival by maximizing exposure of the transplant both to new capillaries growing within and/or around the device (for example by delivery of VEGF) as well as to infused substances that can promote not only growth of new capillaries but also protect/enhance the transplanted cells/tissues (e.g., antiapoptotic substances and/or growth factors such as IGF-I, IGF-II, HGF, GLP-1, Exendin-4, INGAP, Lisophylline, among others).

The invention addresses the problem of rejection of the cellular transplant by providing localized immunosuppression/immunoregulation, which will allow for localized delivery of therapeutic levels of immunosuppressive/immunoregulatory substances, while avoiding the requirement of a long term systemic immunosuppression of the recipient patient, and provides for the addition of factors that favor cell engraftment, growth and function.

More particularly, to achieve the foregoing and other objects, the invention proposes to modify and combine two kinds of devices to provide a hybrid device that allows for a cellular therapy to be performed using implanted devices containing the desired cell or cell composition, coupled with a pump, either external or internal, to locally deliver immunosuppressive/immunoregulatory molecules and/or selected growth factors that will allow survival of the transplanted cells and potentially regeneration/expansion thereof. As will be appreciated, the local delivery of selected factors/cytokines/drugs will facilitate long term survival and function of transplanted cells while minimizing the side effects of recipient immunosuppression.

Thus, in an exemplary embodiment, the invention is comprised of a device to provide a microenvironment favorable to cell survival and function and a pump for local delivery of factors, cytokines and immunosuppressive/immunoregulatory molecules directly to the implanted cells contained in the device. The pump can be external which would generally be preferred for ease of loading of different media cartridges, or internal, such as subcutaneous with a loading port and remote controlled infusion device. Loading of selected agents, preferably by a replaceable/disposable cartridge in an external pump can be tailored to the different requirements of the implanted cellular environment at different times. Exemplary agents include agents for vascularization (e.g., VEGF), anti-inflammatory (e.g., anti-TNFalpa, lysophilline, pentoxyfilline, COX-2 inhibitors, etc.), citoprotective/antiapoptotic agents/molecules, tolerance inducing molecules (e.g., Dr. Terry Strom's power-mix, fusion IL-10, custimulatory blockade, etc.); immunosuppressive agents (e.g., rapamycin, campath-1H, ATG, Prograf, anti IL-2r, MMF, FTY, LEA, etc.); and growth factors (e.g., IGF-I, IGF-II, INGAP, exendin-4, GLP-1, HGF).

The implanted cells can be allogenic or xenogenic islets, alone or in combination with other cell types (e.g., sertoli cells, mesenchimal and bone marrow derived cells, stem cells, etc.). Besides pancreatic islets, which are considered a major target, the strategy of the invention could also be applied to other tissue and cell therapy model systems.

Thus, the invention may be embodied in a device for receiving implanted biological material comprising: a porous outer wall defining an inner space and a fluid manifold assembly for selectively infusing at least one of immunosuppressive and/or growth factor media to said space and a pump or a reservoir for such media, operatively coupled to said manifold assembly. In an exemplary embodiment, the device is a generally flat and potentially slightly curved to maximize loading and re-vascularization while addressing potential cosmetic concerns, particularly for sub-cutaneous placement. The device may however be of cylindrical shape.

The device could be similar to that described in PCT Application No. PCT/MX99/00039 (published as PCT Publication WO 00/35371), in which new capillaries are allowed to grow through a perforated metal mesh, which contains a non-completely occluding plastic (e.g., Teflon) plunger, or could include just the metal mesh element, to allow for re-vascularization of the device content by recipient capillaries that can pass through the mesh. In this latter case, the device would advantageously be implanted in a one step procedure, where the transplanted tissue would be loaded alone, or preferably in conjunction with a matrix or biomaterial that could allow to support viability and function of the transplanted tissue/cells while the re-vascularization process occurs. Such matrix could for example be Biodritin with or without perfluorocarbon (PFC) droplets or a PFC microemulsion (to improve oxygenation of the tissue/cells inside the chamber—see, e.g., Mares-Guia patent on PFC and biodritin, U.S. Pat. No. 6,630, 154). An advantage of the latter embodiment would be to allow implantation of the device in one single operation, instead of two procedures as required by the "plunger" system. In either embodiment, device would include a delivery system that will be the essential component to allow delivery of drugs and nutrients/growth factors.

The invention may also be embodied in a method for implanting biological material in a patient, comprising: providing a device for receiving biological material, said device including a porous outer wall defining an inner space and a fluid manifold assembly for selectively infusing at least one of immunosuppressive and/or growth factor media to said inner space and a pump or a reservoir for such media, operatively coupled to said manifold assembly; implanting said device at a selected location within the patient; allowing tissue ingrowth through said porous outer wall into said inner space; disposing a biological material comprising a selected tissue/cell product within said inner space; and selectively infusing at least one of immunosuppressive and/or growth factor media to said inner space. The implant location may be intraomental (an omental pouch), subcutaneous, or intraperitoneal. In such cases the output of the device would be into the portal system.

BRIEF DESCRIPTION OF THE DRAWINGS

These and other objects and advantages of this invention, will be more completely understood and appreciated by careful study of the following more detailed description of the presently preferred exemplary embodiments of the invention taken in conjunction with the accompanying drawings, in which.

DETAILED DESCRIPTION OF THE INVENTION

Figure 1:
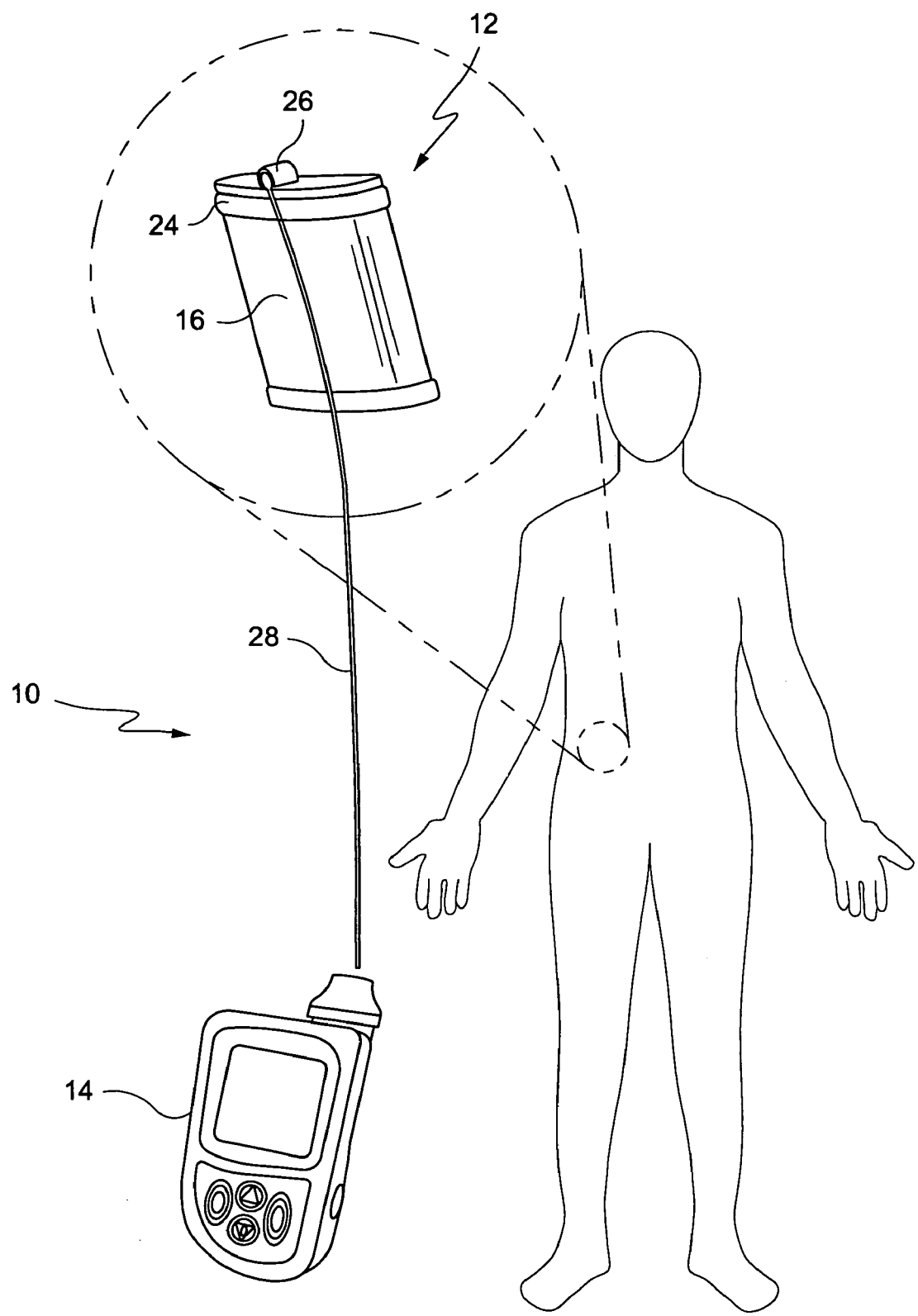
FIG. 1 is a perspective view of a device and pump assembly embodying the invention.
Figure 2:
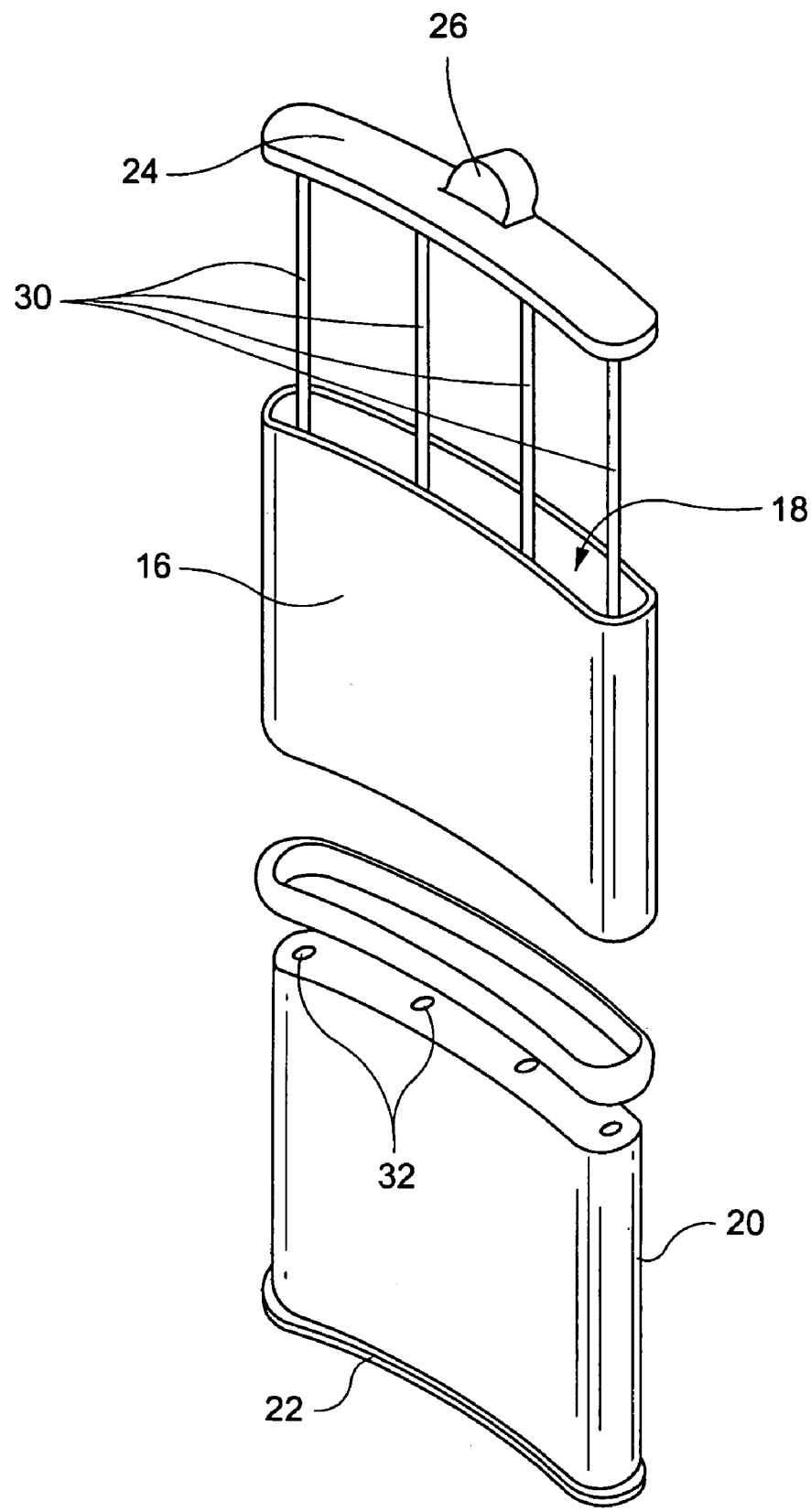
FIG. 2 is an exploded perspective of an embodiment of the device of FIG. 1.

An embodiment of a hybrid device 10 embodying the invention is illustrated by way of example in FIGS. 1 and 2. The hybrid device is comprised of a an implantable device 12 containing a therapeutic tissue/cell product, either at the time of implantation or in a second stage (after pre-vascularization of the device), and an external pump or other reservoir 14 for delivery of selected nutrients, growth factors and immunomodulatory/immunosuppressive substances to improve vascularization, survival, function and growth of the implanted tissues/cells. The implantable device 12 includes a porous outer peripheral wall 16 defining an inner space or cavity 18. The porous outer wall is perforated sufficiently so as to allow for capillaries to grow through the perforations to provide a vascular bed for promoting engraftment of transplanted cells, as described hereinbelow. Thus, the perforations may be, e.g., 300-800 micron, more preferably 400-700 micron. By way of example, a stainless steel mesh with holes around 500 microns may be provided, but the holes could be slightly smaller or bigger.

In one embodiment, during the vascularization phase, a plunger 20 is disposed within the cavity defined by the porous peripheral wall 16 to define a vascularization space or gap with the wall of about 1-2 mm. In this regard, it is preferred that the size of the device be limited, preferably to less than 1 cm altogether in thickness, more preferably, less than 0.7 cm, whereas there is 1 to 2 mm of capillary ingrowth all around the plunger, inside the mesh.

Referring to the illustrated embodiment, one end of the cavity 18 is closed during the vascularization stage with the head or cap 22 of the insert plunger 20 that is selectively disposed within the cavity 18 to define the gap for the new capillaries. A manifold assembly or structure 24 is provided at the opposite end of the device. The manifold structure 24 includes a port 26 for operatively coupling the manifold to a conduit 28 operatively coupled to the pump or reservoir 14, as schematically illustrated in FIGS. 1 and 2, and a manifold cap which serves to distribute the infused media to a plurality of distribution conduits 30 and to close the respective end of the cavity. In the illustrated embodiment, four conduits 30 are provided for distributing media from the manifold cap into the cavity 18 of the device 12. Each of the conduits is advantageously micro-perforated for substantially uniform infusion and distribution of the media within the cavity. The micro-perforations may be uniformly distributed. In the alternative, the micro-perforations may be distributed along the conduit length in a manner to compensate for a decrease in pressure along the length of the conduit in a direction away from the manifold, to ensure uniform distribution of the injected media as described in greater detail below.

It should be noted that in addition to infusion of factors/cytokines/drugs through the manifold structure 24, the outer wall and/or the plunger (if provided) may be coated with a suitable media, such a polymer impregnated with suitable drug(s)/factor(s) to also act as a drug delivery system, particularly when the device is first implanted.

In the embodiment illustrated in FIG. 2, the insert plunger 20 includes longitudinal receptacles 32 disposed for selectively slidably receiving the conduits 30 of the manifold during the vascularization stage. Thus, the plunger 20 can simply be removed in its entirety following the vascularization stage leaving in place the "sprinkler system" defined by the conduits 30 of the manifold 24. A suitable end closure, e.g., a plug corresponding to the external (lower) portion of the plunger is applied to the device to close that end of the cavity following deposition of the cellular media within the cavity defined by the vascularized bed. This plug (not illustrated) can have little recesses for the extremities of the conduits 30 of the "sprinkler system" to lodge.

Figure 3:
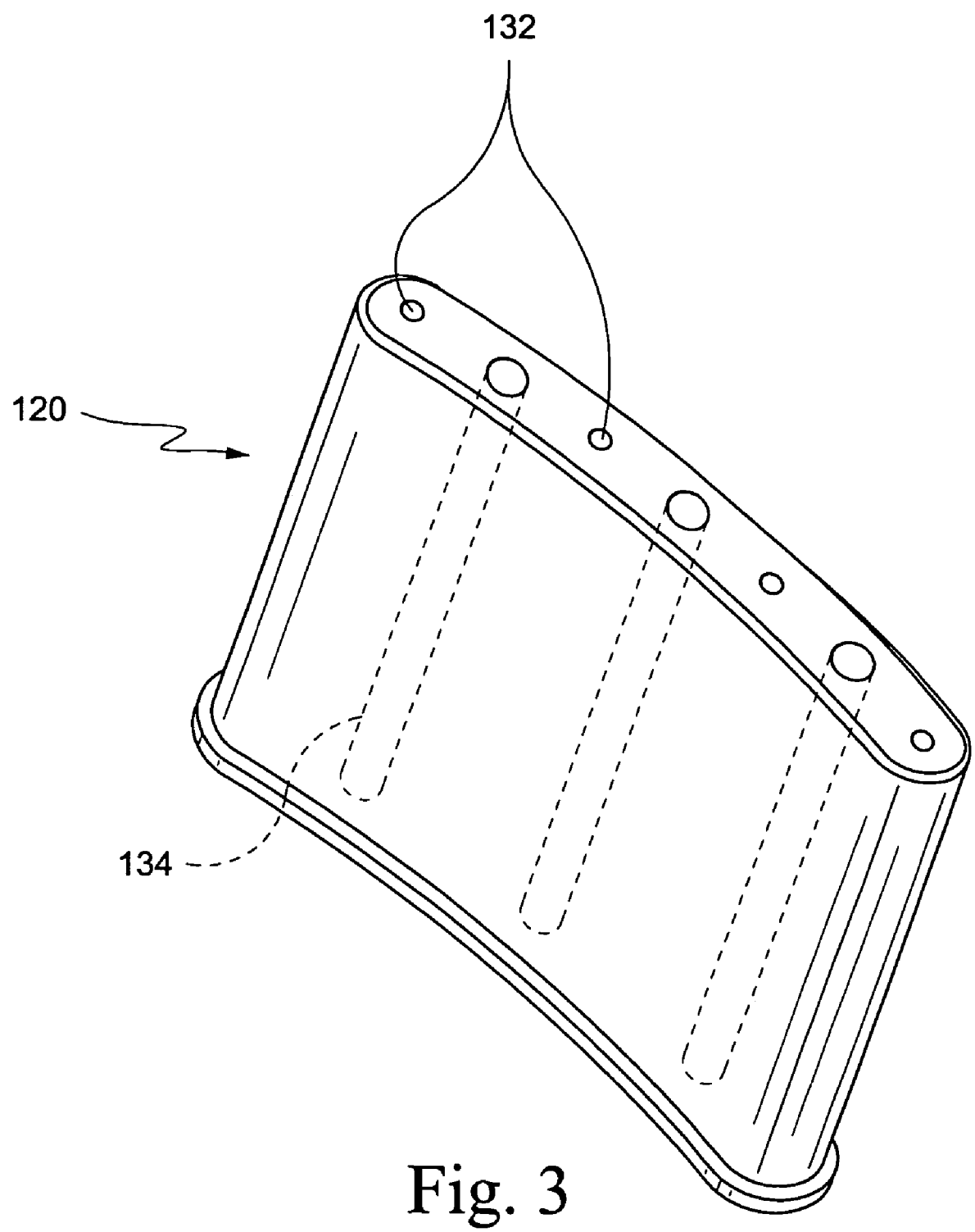
FIG. 3 is a perspective view a plunger component according to an alternative embodiment of the invention.

In the alternative, a manifold assembly is not separately provided and, instead, once the vascularized bed has been formed, the plunger can be replaced with a manifold structure including a manifold cap and conduits of the type illustrated in FIG. 2. In such a case, the end of the cavity opposite the plunger insertion end may be provided as a fixed, preferably perforated, end wall of the device. Moreover, to provide for infusion during the vascularization stage, in accordance with this alternative, the plunger preferably itself includes an infusion manifold assembly, an example of such a plunger being described below with reference to FIG. 3.

Referring again to the embodiment illustrated in FIG. 2, during the vascularization stage, media can be delivered as deemed necessary or desirable through the manifold 24, making use of the pump 14, to distribute the selected media to the respective conduits 30. Because of the presence of the plunger 20 and the respective receptacles 32 for the conduits, the infused media will reverse flow out of the receptacles and be distributed on the outer surface of the plunger 20, within the cavity and, depending upon the stage of capillary formation, may pass through the mesh to the surrounding tissues.

Once the vascularization has sufficiently progressed, the plunger plug is surgically accessed and then slidably displaced from within the cavity. The cells and/or tissues for transplantation are then disposed within the cavity 18 previously occupied by the plunger 20.

A suitable media may be infused to flow between the plunger and the new capillaries to facilitate removal of the plunger. In this regard, with reference to the alternate plunger embodiment of FIG. 3, the assembly could include an infusion system with conduits 134 built into the plunger 120, so that they can be used to infuse solution to facilitate removal of the plunger 120. Such conduit(s) 134 may also be used to deliver the cells/tissue at the time of slow withdrawal of the plunger 120. In this case, the cells/tissue can be progressively loaded while the plunger is slowly withdrawn. Conduits 134 can be provided so as to alternate with the receptacles 132 for the conduits 30 of the "sprinkler system", e.g. three conduits in the plunger 134 interposed with the four conduits 30 of the "sprinkler system", as illustrated. The three conduits 134 of the plunger would thus allow for solution/cell loading while the plunger 120 is removed. In the alternative, e.g., where the plunger does not incorporate conduit(s) for cellular deposit, as in the embodiment of FIG. 2, the tissue/cells can be delivered to the device once the plunger is removed by using a small catheter connected to a syringe (not shown).

In accordance with another embodiment of the invention, the device is implanted already loaded with cells/tissue and without any plunger structure. Thus, in this embodiment, the first, pre-vascularization phase, is omitted, but the manifold assembly 24 and conduits 30, the so-called "sprinkler system", are still used to feed the implanted cells with nutrients and growth factors, while favoring vascularization through the delivery of angiogenic factors.

Where a plunger 20, 120 is provided, and removed following vascularization, the open end of the device is thereafter suitably closed with, e.g., a Teflon closure cap or like closure device, as mentioned above, and the surgical opening is likewise suitably closed. Thereafter, anti-inflammatory, immunosuppression or other agents/molecules may be infused using the pump and distributed via the manifold 24 and distribution conduits 30 to the transplanted cells and tissues. As will be appreciated, the generally flat thin configuration of the device contributes to the delivery of the nutrients from the new capillaries to the deposited cells. Moreover, the infusion of suitable media via the manifold and distribution conduits ensures proper support of the implanted cells as well as provides effective localized immunosuppresion to preclude rejection by the host immune system. Because the immunosuppression is localized to the implanted cells, systemic immunosuppression may not be required, or may be required only short term peri-transplant, or may be required at significantly lower doses compared to currently used systemic immunosuppression. The doses locally delivered may be controlled so that, to the extent the immunosuppressive drugs are transported via the new capillaries to elsewhere in the patient's body, the concentration would be such as to minimize any adverse affect on the patient.

The porous device wall 16 is preferably wide, generally flat and narrow, as illustrated, with rounded ends so as to be relatively ergonomic, to be comfortable to the patient while implanted and to minimize stress concentration. The device, however, may assume a broader configuration and may even take a cylindrical form, provided the conduits 30 of the infusion manifold suitably distribute nutrients and other media to the core where the nutrients delivered by the new capillaries will not reach.

The porous outer wall can be of stainless steel, polymer or any other suitable material that will provide dimensional stability thereto as a cavity defining member and which will provide the necessary porosity for capillary/tissue ingrowth. The length of the porous section may be any suitable length and width according to the therapeutic needs in order to adequately favor the production of the biological factor to be provided by the implanted cells and may be thus the device may be around 3 to 15 centimeters in length and width. This would be a typical range for a device containing cells that deliver a therapeutic product (e.g. islet cells delivering insulin). However, larger devices may be required for implantation of hepatocytes, for example, where the volume of cells to be implanted to support life (e.g., in a situation of device implantation for bridging between liver failure and regeneration of the native liver, or between liver failure and allergenic liver transplantation. In these cases the device could be built to house up to 100-200 ml of cell/tissue volume, therefore requiring larger dimensions. In the case of islets the total packed cell volume transplanted could be less that 15 cc of cell/tissue, and typically less that 7 cc of tissue.

As will be appreciated, the degree of porosity of the outer wall will determine the size of the neo-formed vessels in the vascular bed. For this reason, the size of the mesh or pores may be determined according to the target application of the encapsulated structure.

The closure caps or plugs defined at the respective longitudinal ends of the device have a length suitable for the function of sealing to e.g., the porous wall and may be for example 10% of the length of the device, while having transverse dimensions similar to those of the porous body. If deemed necessary or desirable, additional fastening elements may be provided to suitably secure the plunger, manifold, and/or other end cap in place.

The plunger unit 20, 120, is preferably a solid component having a shape generally corresponding to that of the perforate wall 16 but in each direction reduced so as to define a gap with the perforate wall. The plunger may however have a slightly different shape that the outer perforate wall to facilitate insertion and removal. Thus, the walls of the plunger may be slightly tapered in the insert direction and/or may be grooved or surface treated to facilitate removal. The plunger can be solid or hollow, although solid (except for manifold conduit receptacles and/or it's own infusion manifold) is preferred for dimensional accuracy and to minimize the likelihood of media passing into the inside of the plunger and then potentially decomposing over time.

In use, the thickness of the vascular bed formed by the encapsulation of the device 12 and capillary growth through the porous wall 16 depends on the gap between the porous body 16 and the plunger 20, 120, the spacing being determined according to the requirements arising from the end use of the encapsulated device. The transverse dimension of the porous body and the plunger are chosen in accordance with the volume and thickness required from 4 to 15 mm with a separation or gap of 1 to 2 mm.

In accordance with an embodiment of the invention, the procedure for creating a vascular bed to define a reservoir for receiving biological material and for facilitating long term survival and function of the transplanted cells is comprised of implanting the device in the body of the patient with the plunger (when provided) disposed inside the porous wall to define a gap for tissue ingrowth. One end of the device is closed by the head of the plunger, if provided, or plugged or integrally closed, and the other end of the device is closed or is capped, e.g., with the manifold unit (or closed in case the mandrel is later substituted for the plunger or incorporated in it). The implant location may be intraomental (an omental pouch), subcutaneous, or intraperitoneal, whereby the output of the device is into the portal system.

When implanted in this way, the porous body is overlaid with fibrocollagen by the natural action of the patient's body and a vascular bed develops in the gap between the plunger and the porous wall by virtue of the encapsulation and tissue ingrowth. The tissue ingrowth or vasularization stage may be facilitated or enhanced by infusing suitable factors through the manifold structure using the pump. In addition or in the alternative, the outer wall and/or the plunger may be coated with a suitable media, such a polymer impregnated with suitable drug(s)/factor(s) to act as a drug delivery system.

Subsequently, once the fibrocollagen layer has been formed, a partial incision is made in order to expose the plunger access end of the device in order to remove it. If deemed necessary or desirable, suitable media may be infused through the manifold structure to facilitated plunger removal. When the plunger is removed, a neovascularized receptacle is defined and is suitable for implantation of biological factor producing cells through the opening in the end of the device. The biological material, made up of the biological factor producing cells and optionally a culture medium, selected in accordance with the type of cell to be implanted, is disposed within the receptacle defined by the space left empty by removal of the plunger. The device is then closed with an appropriate sealing element in such a way that the neovascularized receptacle is closed within the patient. The biological factor promoter cells act in contact with the neovascularized tissues and the biological factor is absorbed by the bloodstream. Concurrently, immunosuppressive/immunoregulatory molecules and/or selected growth factors that will allow survival of the transplanted cells and potentially regeneration/expansion are infused through the manifold structure. As will be appreciated, the local delivery of selected factors/cytokines/drugs will facilitate long term survival and function of transplanted cells while minimizing the side effects of recipient immunosuppression.

To further increase the effectiveness of the treatment, factor producing cells that have been genetically manipulated by known techniques can be used. The amount of cells in the case of treatment of diabetes referred to hereinabove is 6,000 to 12,000 islets of Langerhans per kilogram of the patient's weight. In the case of the invention, these can be combined with Sertolli cells in order to immunologically protect them from rejection. In addition, or in the alternative, the cells disposed inside the device can include cells that produce substances with a therapeutic activity as in the case of thyroid and parathyroid cells, among others.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims. For example, in an alternative configuration, as mentioned above, the device could be implanted without the plunger, already containing the cells/tissue, without providing for a first phase of vascularization between mesh and plunger, but using the "sprinkler system" to feed the implanted cells with nutrients and growth factors, while favoring re-vascularization through the delivery of angiogenic factors.

What is claimed is:

1. A device for receiving implanted biological material and configured for implantation into a patient, wherein said device comprises:
   a) a porous outer wall defining an inner space, said inner space providing a receptacle for implanted biological material comprising a selected tissue/cell product, said inner space sized to receive 6,000 to 12,000 cells per kilogram of the weight of the patient, and said outer wall having a porosity which permits vasculature to reach the implanted biological material from outside the porous outer wall;
   b) a fluid manifold assembly for selectively infusing at least one of immunosuppressive and/or growth factor media to said inner space, wherein said manifold assembly includes at least one longitudinally disposed media distribution conduit for distributing media to said inner space, and wherein microperforations along the length of said conduit compensate for a decrease in pressure along the length of the conduit in a direction away from the manifold for substantially uniform infusion and distribution of the media within said inner space; and
   c) a pump or a reservoir for such media, operatively coupled to said manifold assembly.

2. A device as in claim 1, further comprising a removable plunger body for being disposed in said inner space so as to define a peripheral gap between the plunger and the outer wall.

3. A device as in claim 2, wherein said manifold assembly is formed separately from said plunger body, and said plunger body and said manifold assembly are selectively interchangeably placed within said inner space.

4. A device as in claim 2, wherein the plunger body and the manifold assembly are complementarily configured for simultaneous placement within the inner space.

5. A device as in claim 4, wherein said manifold assembly includes a closure cap.

6. A device as in claim 4, wherein there is a plurality of distribution conduits.

7. A device as in claim 4, wherein the manifold assembly and the plunger body are selectively inserted into said inner space from opposite longitudinal ends of said device.

8. A device as in claim 7, wherein the plunger body has built-in conduits operatively coupled to said pump or reservoir, wherein said conduits are capable of delivering a physiologic solution or a selected tissue/cell product to said inner space at the time of removal of the plunger, either to facilitate plunger displacement or to simultaneously load the selected cell product.

9. A device as in claim 8, wherein the built-in conduits of the plunger body are selectively positioned parallel and alternating with the conduits of the manifold assembly.

10. A device as in claim 1, wherein said manifold assembly includes a closure cap.

11. A device as in claim 1, wherein there is a plurality of distribution conduits.

12. A device as in claim 1, wherein the porous outer wall has first and second, generally parallel side walls.

13. A device as in claim 12, wherein said parallel side walls are curved.

14. A device as in claim 12, wherein the porous outer wall has third and fourth, convexly curved side walls.

15. A method for implanting biological material in a patient, comprising:
   a) providing a device for receiving biological material, said device comprising:
      i) a porous outer wall defining an inner space, said inner space providing a receptacle for implanted biological material comprising a selected tissue/cell product, said inner space sized to receive 6,000 to 12,000 cells per kilogram of the weight of the patient, and said outer wall having a porosity which permits vasculature to reach the implanted biological material from outside the porous outer wall;
      ii) a fluid manifold assembly for selectively infusing at least one of immunosuppressive and/or growth factor media to said inner space, wherein said manifold assembly includes at least one longitudinally disposed media distribution conduit for distributing media to said inner space, and wherein microperforations along the length of said conduit compensate for a decrease in pressure along the length of the conduit in a direction away from the manifold for substantially uniform infusion and distribution of the media within said inner space; and
      iii) a pump or a reservoir for such media, operatively coupled to said manifold assembly;
   b) implanting said device at a selected location within the patient;
   c) allowing tissue ingrowth through said porous outer wall into said inner space;
   d) disposing the biological material comprising a selected tissue/cell product within said inner space; and
   e) selectively infusing at least one of immunosuppressive and/or growth factor media to said inner space.

16. A method as in claim 15, wherein said implanting comprises implanting said device in a location selected from the group consisting of intraomental, subcutaneous, and intraperitoneal.

17. A method as in claim 15, wherein the device further comprises iv) a removable plunger body within said inner space so as to define a peripheral gap between the plunger and the outer wall, such that said tissue ingrowth is into said peripheral gap.

18. A method as in claim 17, further comprising after step c) allowing tissue ingrowth, and before step d) disposing a biological material, a step c') removing said plunger.

19. A method as in claim 15, wherein step d) disposing a biological material precedes step b) implanting said device.

20. A method for implanting biological factor producing biological material in a patient, comprising:
   a) providing a device for receiving biological factor producing biological material, said device comprising:
      i) a porous outer wall defining an inner space, said inner space providing a receptacle for implanted biological material comprising a selected tissue/cell product, said inner space sized to receive 6,000 to 12,000 cells per kilogram of the weight of the patient, and said outer wall having a porosity which permits vasculature to reach the implanted biological material from outside the porous outer wall;
      ii) a fluid manifold assembly for selectively infusing at least one of immunosuppressive and/or growth factor media to said inner space, wherein said manifold assembly includes at least one longitudinally disposed media distribution conduit for distributing media to said inner space, and wherein microperforations along the length of said conduit compensate for a decrease in pressure along the length of the conduit in a direction away from the manifold for substantially uniform infusion and distribution of the media within said inner space;
      iii) a pump or a reservoir for such media, operatively coupled to said assembly; and
      iv) a structure defining a path for the biological factor produced by said biological material to be conducted to the patient's circulatory system;
   b) implanting said device at a selected location within the patient;
   c) disposing the biological factor producing biological material comprising a selected tissue/cell product within said inner space; and
   d) selectively infusing at least one of immunosuppressive and/or growth factor media to said inner space using said assembly.

21. A method as in claim 20, further comprising, after step b) implanting said device, a step b') allowing tissue ingrowth through said porous outer wall into said inner space.

22. A method as in claim 21, wherein the device further comprises v) a removable plunger body within said inner space so as to define a peripheral gap between the plunger and the outer wall, such that said tissue ingrowth is into said peripheral gap.

23. A method as in claim 22, further comprising after step b') allowing tissue ingrowth, and before step c) disposing the biological factor producing biological material, a step b") removing said plunger.

24. A method as in claim 20, wherein step c) disposing the biological factor producing biological material precedes step b) implanting said device.

25. A method for promoting the survival of biological material, comprising:
   a) providing the device as in claim 1;
   b) disposing a biological material comprising a selected tissue/cell product within said inner space; and
   c) selectively infusing at least one of immunosuppressive and/or growth factor media to said inner space.

26. The method as in claim 25, wherein the method is ex vivo.

27. The method as in claim 26, further comprising allowing tissue ingrowth through said porous outer wall into said inner space.

28. The method as in claim 26, further comprising, before step b) disposing a biological material, step a') allowing tissue ingrowth through said porous outer wall into said inner space.

29. The method as in claim 28, wherein the device of claim 1 further comprises d) a removable plunger body within said inner space so as to define a peripheral gap between the plunger and the wall, such that said tissue ingrowth is into said peripheral gap.

30. The method as in claim 29, further comprising after step a') allowing tissue ingrowth, and before step b) disposing a biological material, step a") removing said plunger.

31. The method as in any one of claims 26-30, wherein said biological material is a biological factor producing biological material.

32. The method as in claim 25, wherein the method is in vivo, and wherein the method further comprises:
   d) implanting said device at a selected location within a subject; and
   e) allowing tissue ingrowth through said porous outer wall into said inner space.

33. The method as in claim 32, wherein said implanting comprises implanting said device in a location selected from the group consisting of intraomental, subcutaneous, and intraperitoneal.

34. The method as in claim 32, wherein the device of claim 1 further comprises d) a removable plunger body within said inner space so as to define a peripheral gap between the plunger and the wall, such that said tissue ingrowth is into said peripheral gap.

35. The method as in claim 34, further comprising a step e') removing said plunger, wherein step d) implanting said device, step e) allowing tissue ingrowth, and step e') removing said plunger occur before step b) disposing a biological material.

36. The method as in any one of claims 32-35, wherein said biological material is a biological factor producing biological material.

* * * * *